United States Patent
Adje et al.

(10) Patent No.: US 6,737,433 B1
(45) Date of Patent: May 18, 2004

(54) 1-N-PHENYLAMINO-1H-IMIDAZOLE DERIVATIVES AS AROMATASE INHIBITORS AND PHARMACEUTICAL COMPOSITIONS CONTAINING THEM

(75) Inventors: Nathalie Adje, Genas (FR); Paule Bonnet, Menton (FR); Denis Carniato, Marcoussis (FR); Remi Delansorne, Nice (FR); Jean Lafay, Nice (FR); Jean-Claude Pascal, Nice (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 10/319,840

(22) Filed: Dec. 16, 2002

(51) Int. Cl.$^7$ .................. A61K 31/4164; C07D 233/88
(52) U.S. Cl. ..................... 514/398; 548/331.1
(58) Field of Search ............. 548/331.1; 514/398

(56) References Cited

U.S. PATENT DOCUMENTS

| | | | |
|---|---|---|---|
| 4,361,575 A | * 11/1982 | Stahle et al. | 514/398 |
| 4,908,363 A | * 3/1990 | Klotzer et al. | 514/235.8 |
| 5,071,861 A | 12/1991 | Bowman et al. | |
| 5,703,109 A | 12/1997 | Karjalainen et al. | |

FOREIGN PATENT DOCUMENTS

| | | |
|---|---|---|
| EP | 641785 | 2/1995 |
| EP | 640595 | 3/1995 |

OTHER PUBLICATIONS

Brodie et al, "Aromatase Inhibitors and their Application in Breast Cancer Treatment", Dept. of Pharmacology etc., pp. 171–179, 1999.

Pritchard, "Current and Future Directions in Medical Therapy for Breast Carcinoma", American Cancer Society, pp. 3065–3072, 2000.

Njar et al, "Comprehensive Pharmacology and Clinical Efficacy of Aromatose Inhibitors", Dept. of Pharmacology etc., pp. 233–255, 1999.

Bulun et al, "Endocrine Disorders Associated with Inappropriately High Aromatase Expression", Steroid Biochem, pp. 133–139, 1996.

Sasano et al, "Intratumoral Aromatase in Human Breast, Endometrial, and Ovarian Malignancies", Endocrine Reviews, pp. 593–607, 1998.

Auclerc et al, "Management of Advanced Prostate Cancer", The Oncologist, pp. 36–44, 2000.

* cited by examiner

*Primary Examiner*—Laura L. Stockton
(74) *Attorney, Agent, or Firm*—Dennison, Schultz, Dougherty & MacDonald

(57) ABSTRACT

Imidazole derivatives of the formula:

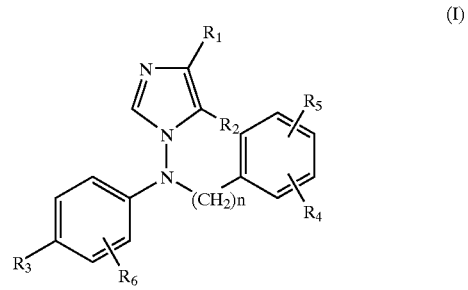

(I)

in which
$R_1$ and $R_2$ are each independently hydrogen, $(C_1-C_6)$ alkyl or $(C_3-C_8)$cycloalkyl;
n is 0, 1 or 2;
$R_3$, $R_4$, $R_5$ and $R_6$ are each independently hydrogen or a $(C_1-C_6)$alkyl, halogen, cyano, $(C_1-C_6)$alkoxy, trifluoromethyl, $(C_1-C_6)$alkylthio, $(C_1-C_6)$ alkylsulfonyl, sulfonamido, acyl, $(C_1-C_6)$ alkoxycarbonyl, or carboxamido group;
$R_3$ and $R_6$ together with the phenyl ring bearing them can also form a benzofurane, or a N-methylbenzotriazole. The invention also relates to pharmaceutical compositions containing these derivatives, and to the uses thereof.

32 Claims, No Drawings

1-N-PHENYLAMINO-1H-IMIDAZOLE DERIVATIVES AS AROMATASE INHIBITORS AND PHARMACEUTICAL COMPOSITIONS CONTAINING THEM

BACKGROUND OF THE INVENTION

The present invention relates to 1-N-phenylamino-1H-imidazole derivatives as aromatase inhibitors and to pharmaceutical compositions containing them.

Aromatase is the physiological enzyme responsible for the specific conversion of androgens such as androstenedione or testosterone, into estrogens such as estrone and estradiol, respectively (Simpson E R et al., Endocrine Reviews, 1994, 15: 342–355). Inhibition of aromatase iso, therefore, a strategy of choice to interfere with normal or pathological estrogen-induced or estrogen-dependent biological processes such as female sexual differentiation, ovulation, implantation, pregnancy, breast and endometrial cell proliferation as well as regulation of spermatogenesis or prostate cell proliferation in male or of non-reproductive functions such as bone formation or immune T cell and cytokine balance (Simpson E R et al., Recent Progress in Hormone Research, 1997, 52: 185–213 and the whole issues of Endocrine Related Cancer (1999, volume 6, n° 2) and Breast Cancer Research Treatment (1998, volume 49, supplement n° 1)).

A large number of azole derivatives are known as antifungal agents. Some imidazole or triazole derivatives have already been described as inhibitors of the enzyme aromatase. Generally, the imidazolyl or the triazolyl group is associated with aromatic rings as found in letrozole (EP-A-236 940; Lamb H M and Adkins J C, Drugs, 1998, 56: 1125–1140):

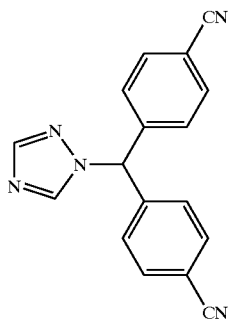

or anastrozole (EP-A-296 749; Wiseman L R and Adkins J C, Drugs Aging, 1998, 13: 321–332):

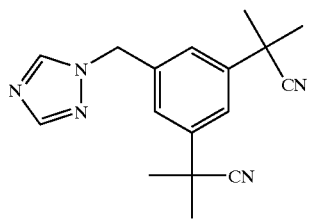

Imidazoles or triazoles linked via a methylene group to a benzotriazole are described in EP-A-293 978:

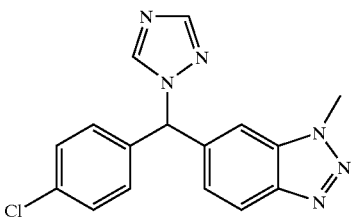

Diterbutyl phenols having a N-amino-imidazole moiety in the para position are described in U.S. Pat. No. 4,908,363 and are presented as having inflammation-inhibiting and oedema-inhibiting properties:

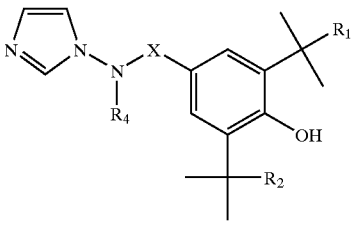

More recently, M. OKADA et al. (Chem. Pharm. Bull., 44 (10), 1996, 1871–1879) described a series of [4-(bromophenylmethyl)-4-(cyanophenyl)amino]-azoles and their azine analogs:

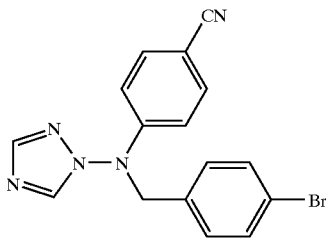

YM 511

SUMMARY OF THE INVENTION

It has now been found that imidazole derivatives which invariably contain a 1-[N-phenylamino]group demonstrate an unexpectedly high potency to inhibit aromatase.

Accordingly, one object of this invention is to provide 1-[N-phenylamino]imidazole derivatives which are potent aromatase inhibitors.

Another object of this invention is to provide a pharmaceutical composition containing, as active ingredient, a 1-[N-phenylamino]imidazole derivative as depicted below or a pharmaceutically acceptable acid addition salt thereof.

A further object of this invention is to provide the use of a 1-[N-phenylamino]imidazole derivative in the manufacture of a medicament intended for treating or preventing various diseases and for managing reproductive functions in women, in men as well as in female and male wild or domestic animals.

The 1-[N-phenylamino]imidazole derivatives of this invention are represented by the following general formula (I):

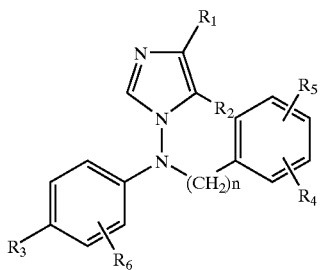

and acid addition salts, solvates and stereoisomeric forms thereof, wherein:

R₁ and R₂ are each independently hydrogen, a (C₁–C₆)alkyl or a (C₃–C₈)cycloalkyl;

n=0, 1, 2;

R₃, R₄, R₅ and R₆ are each independently hydrogen, or a (C₁–C₆)alkyl, halogen, cyano, (C₁–C₆)alkoxy, trifluoromethyl, (C₁–C₆)alkylthio, (C₁–C₆)alkylsulfonyl, sulfonamido, acyl, (C₁–C₆)alkoxycarbonyl, or carboxamido group;

R₃ and R₆ together with the phenyl ring bearing them can also form a benzofurane or a N-methylbenzotriazole.

DETAILED DESCRIPTION OF THE INVENTION

In the description and claims, the term "(C₁–C₆)alkyl" is understood as meaning a linear or branched hydrocarbon chain having 1 to 6 carbon atoms. A (C₁–C₆)alkyl radical is for example a methyl, ethyl, propyl, isopropyl, butyl, isobutyl, tert-butyl, pentyl, isopentyl or hexyl radical.

The term "halogen" is understood as meaning a chlorine, bromine, iodine or fluorine atom.

The term "(C₃–C₈)cycloalkyl" is understood as meaning a saturated monocyclic hydrocarbon having 3 to 8 carbon atoms. A (C₃–C₈)cycloalkyl radical is for example a cyclopropyl, cyclobutyl, cyclopentyl, cyclohexyl, cycloheptyl or cyclooctyl radical.

The term "(C₁–C₆)alkoxy" is understood as meaning a group OR in which R is a (C₁–C₆)alkyl as defined above. A (C₁–C₆)alkoxy radical is for example a methoxy, ethoxy, propoxy, isopropoxy, butoxy, isobutoxy, tert-butoxy, n-pentyloxy or isopentyloxy radical.

The term "acyl" is understood as meaning a group

in which R' is hydrogen or a (C₁–C₆)alkyl as defined above.

Compounds of formula (I) form acid addition salts, for example with inorganic acids such as hydrochloric acid, hydrobromic acid, sulfuric acid, nitric acid, phosphoric acid and the like or with organic carboxylic acids such as acetic acid, propionic acid, glycolic acid, pyruvic acid, oxalic acid, malic acid, fumaric acid, tartaric acid, citric acid, benzoic acid, cinnamic acid, mandelic acid, methanesulfonic acid and the like.

Preferred compounds of formula (I) are those wherein:

n is 0 or 1;

R₁ and R₂ are each independently hydrogen or (C₁–C₆)alkyl;

R₃ is cyano or trifluoromethyl;

R₄ is hydrogen, (C₁–C₆)alkyl, halogen, cyano, (C₁–C₆)alkoxy, trifluoromethyl, (C₁–C₆)alkylthio, (C₁–C₆)alkylsulfonyl or (C₁–C₆)alkoxycarbonyl;

R₅ is hydrogen, halogen, (C₁–C₆)alkoxy or trifluoromethyl;

R₆ is hydrogen;

or R₃ and R₆ together with the phenyl ring form a N-methylbenzotriazole.

Also preferred are the compounds of formula (I) wherein:

n is 0 or 1;

R₁, R₂ and R₆ are each hydrogen;

R₄ is halogen, cyano or trifluoromethyl.

Especially preferred compounds of formula (I) are those wherein R₃ is cyano; those wherein R₅ is hydrogen or trifluoromethyl; and those wherein n is 1.

Valuable compounds are selected from the group consisting of:

4-[N-(1H-imidazol-1-yl)-N-(4-trifluoromethylphenylmethyl)amino]benzonitrile

4-[N-(1H-imidazol-1-yl)-N-(4-chlorophenylmethyl)amino]benzonitrile,

4-[N-(1H-imidazol-1-yl)-N-(4-cyanophenylmethyl)amino]benzonitrile, 4,4'-[N-(1H-imidazol-1-yl)amino]bis-benzonitrile, 4-[N-(1H-imidazol-1-yl)-N-(4-fluorophenylmethyl)amino]benzonitrile, 4-[N-(1H-imidazol-1-yl)-N-(3,4-difluorophenylmethyl)amino]benzonitrile, and the acid addition salts, solvates or stereoisomeric forms thereof.

By virtue of their capability to inhibit aromatase, and thus to exhaust all sources of endogenous estrogens, the compounds of the present invention can be used alone or in combination with other active ingredients for the treatment or the prevention of any estrogen-dependent disorder or for the management of estrogen-regulated reproductive functions, in humans as well as in wild or domestic animals.

The breasts being sensitive targets of estrogen-stimulated proliferation and/or differentiation, inhibitors of aromatase are especially useful in the treatment or prevention of benign breast diseases in women, gynecomastia in men and in benign or malignant breast tumors with or without metastasis both in men and women (Brodie A M and Njar V C, Steroids, 2000, 65: 171–179; Pritchard K I, Cancer, 2000, 85, suppl 12: 3065–3072), or in male or female domestic animals.

Due to the involvement of estrogens in the mechanisms of ovulation, implantation and pregnancy, inhibitors of aromatase according to the invention can be used, respectively, for contraceptive, contragestive or abortive purposes in women (Njar V C and Brodie A M, Drugs, 1999, 58: 233–255) as well as in females of wild or domestic animal species.

The uterus is another reproductive organ responsive to estrogenic stimulation and inhibition of aromatase is therefore useful to treat or prevent endometriosis, benign uterine diseases or benign or malignant uterine tumors with or without metastasis in women (Njar V C and Brodie A M, Drugs, 1999, 58: 233–255) or in female domestic animals.

The ovary being the physiological source of estrogen, inhibitors of aromatase can be used to treat abnormal or untimely ovarian estrogen production such as polycystic ovary syndrome or precocious puberty, respectively (Bulun et al., J Steroid Biochem Mol Biol, 1997, 61: 133–139). Ovarian as well as non-ovarian but estrogen-producing benign or malignant tumors with or without metastasis (Sasano H and Harada N, Endocrine Reviews, 1998, 19: 593–607) may also benefit from treatment with aromatase inhibitors according to the invention.

In males, prostate and testicular tissues are also responsive to estrogenic stimulation (Abney T O, Steroids, 1999, 64: 610–617; Carreau S et al., Int J Androl, 1999, 22: 133–138). Therefore, aromatase inhibitors can be used to treat or to prevent benign (Sciarra F and Toscano V, Archiv Androl, 2000, 44: 213–220) or malignant prostate tumors with or without metastasis (Auclerc G et al., Oncologist, 2000, 5: 36–44) or to treat, prevent or control spermatogenesis functions or malfunctions, in men as well as in male wild or domestic animals.

Estrogens are also known to be implicated in the regulation of bone turnover; therefore, aromatase inhibitors may be useful, alone or in combination with other antiresorbtive or proosteogenic agents, in the treatment or prevention of bone disorders according to appropriate therapeutic sequences or regimens.

In addition, estrogens are involved in the regulation of the balance between $Th_1$ and $Th_2$ predominant immune functions and may therefore be useful in the treatment or prevention of gender-dependent auto-immune diseases such as lupus, multiple sclerosis, rheumatoid arthritis and the like.

When the compounds of formula (I) are administered for the treatment or prevention of estrogen-dependent disorders, they can be combined with one or several other sexual endocrine therapeutic agents. In the case of the control or management of reproductive functions such as male or female fertility, pregnancy, abortion or delivery, the compounds of formula (I) can be combined with for example a LH-RH agonist or antagonist, an estroprogestative contraceptive, a progestin, an anti-progestin or a prostaglandin. When the compounds of formula (I) are intended for the treatment or prevention of benign or malignant diseases of the breast, the uterus or the ovary, they can be combined with e.g. an anti-estrogen, a progestin or a LH-RH agonist or antagonist. In the case of the treatment or prevention of benign or malignant diseases of the prostate or the testis, the compounds of formula (I) can be combined with for example an antiandrogen, a progestin, a lyase inhibitor or a LH-RH agonist or antagonist.

The term "combined" refers herein to any protocol for co-administration of a compound of formula (I) and one or more other pharmaceutical substances, irrespective of the nature of the time of administration and the variation of dose over time of any of the substances. The co-administration can for example be parallel or sequential.

The invention thus also relates to a method of treating or preventing the above-mentioned diseases, comprising the administration to a subject in need thereof of a therapeutically effective amount of a compound of formula (I) or a pharmaceutically acceptable acid addition salt thereof, optionally in combination with another active ingredient.

For the treatment/prevention of any of these diseases, the compounds of formula (I) may be administered, for example, orally, topically, parenterally, in dosage unit formulations containing conventional non-toxic pharmaceutically acceptable carriers, adjuvants and vehicles. These dosage forms are given as examples, but other dosage forms may be developed by those skilled in the art of formulation, for the administration of the compounds of formula (I). The term parenteral as used herein includes subcutaneous injections, intravenous, intramuscular, intrastemal injection or infusion techniques. In addition to the treatment of humans, the compounds of the invention are effective in the treatment of warm-blooded animals such as mice, rats, horses, cattle sheep, dogs, cats, etc.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

They may also be coated by the technique described in U.S. Pat. Nos. 4,256,108; 4,166,452 and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents, for example a naturally-occurring phosphatide, such as lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occuring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage levels of the order of from about 0.0001 mg to about 1 mg/kg of body weight per day are useful in the treatment of the above-indicated conditions, or alternatively about 0.1 mg to about 10 mg per patient per day.

The amount of active ingredient that may be combined with the carrier materials to produce a single dosage form will vary depending upon the host treated and the particular mode of administration. Dosage unit forms will generally contain between from about 1 mg to about 100 mg of active ingredient, typically 2 mg, 5 mg, 10 mg, 20 mg, 40 mg, 50 mg, 60 mg, 80 mg, or 100 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The 1-N-phenyl-amino-1H-imidazole derivatives of formula (I) of the invention and their acid addition salts can be prepared following the general scheme 1.

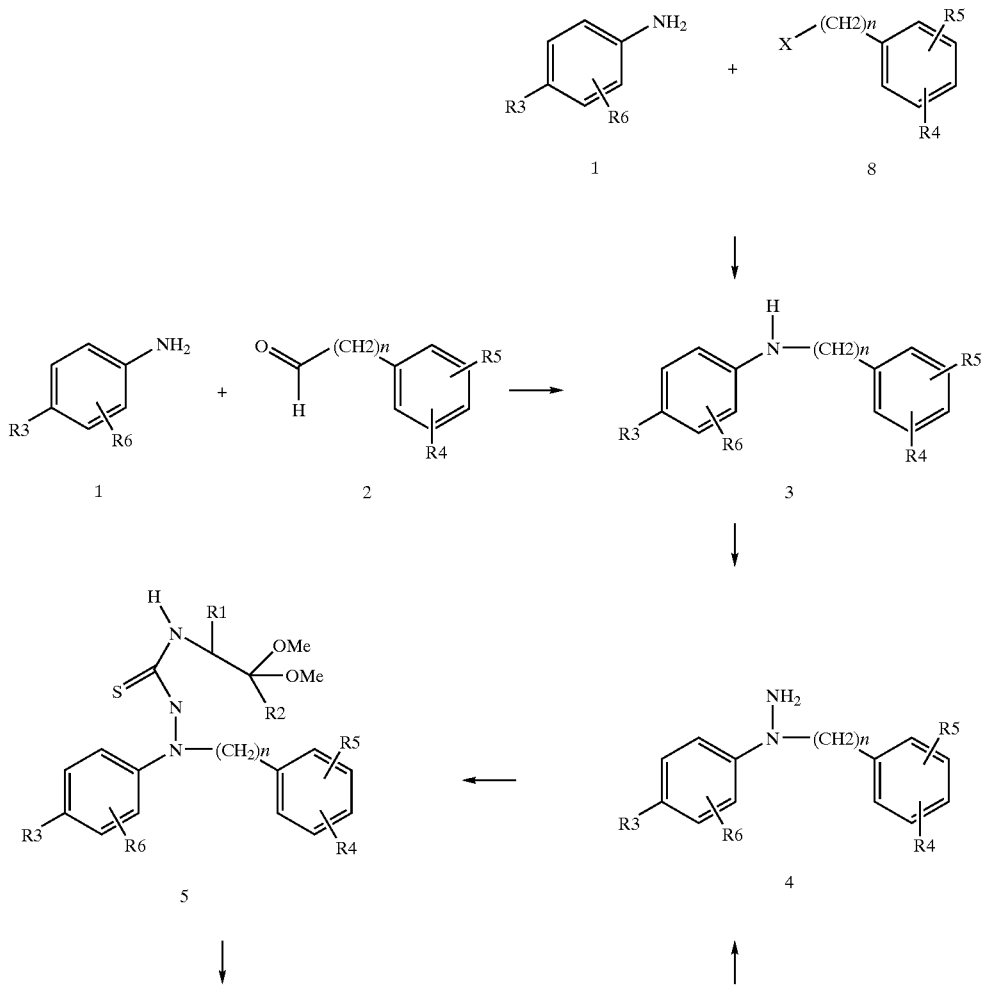

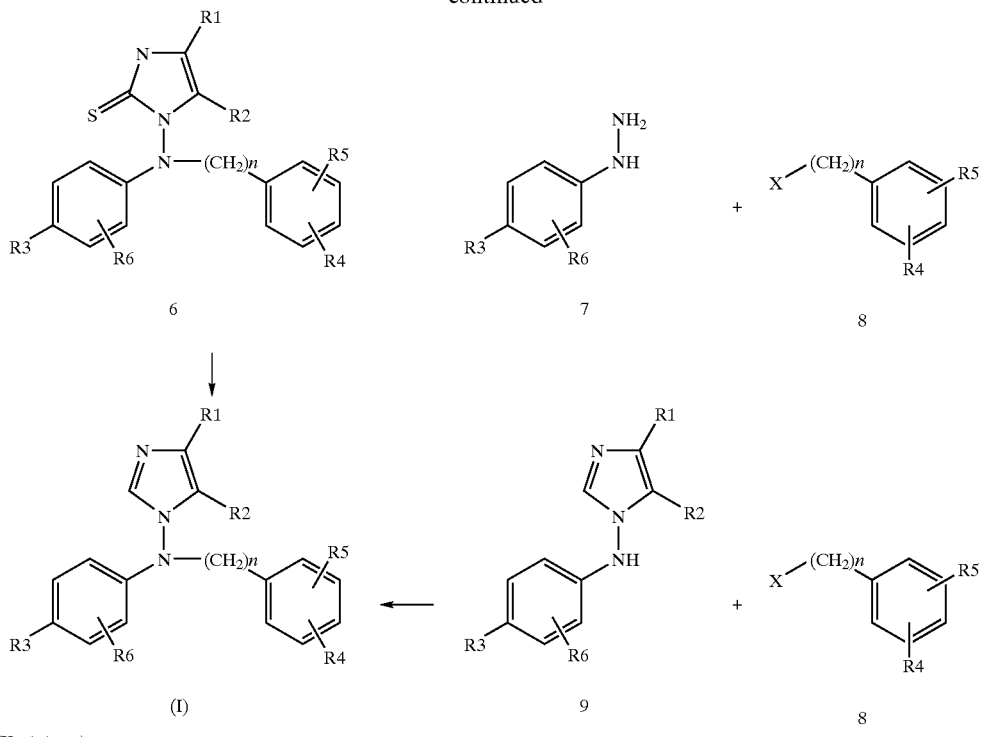

(I)

(X = halogen)

According to scheme 1 aniline derivative (1) is condensed with the aldehyde of formula (2) and the imine intermediate is reduced with sodium borohydride or hydrogenated using palladium or platinium oxide as catalyst to afford the N,N-disubstituted aniline (3). Said aniline (3) can also be prepared by reaction of a halogeno derivative (8) with an aniline of formula (1).

The N,N-disubstituted aniline (3) is converted to its nibroso derivative using standard conditions, then reduced to afford the 1,1-disubstituted hydrazine of formula (4).

Alternatively, the 1,1-disubstituted hydrazine (4) can be prepared by selective N-alkylation of a compound of formula (7) with a compound of formula (8) using the conditions described by U. LERCH and I. KÖNIG (*Synthesis*, 1983, 2, 157–8).

Then, condensation of (4) with dialkyloxy-alkyl-isothiocyanate derivatives or ethylenedioxy-alkyl-isocyanate derivatives, affords the thiosemicarbazide (5) which is transformed to the 1-amino-imidazole-2-thione (6) by treatment with an acid like acetic acid or sulphuric acid.

Desulfurization of (6) in acetic acid, following the conditions described by S.GRIVAS and E.RONNE in *Acta Chemica Scandinavia*, 1995, 49, 225–229, gives the final 1-N-phenylamino-1H-imidazole derivative (I), which is optionally converted to one of its pharmaceutically acceptable acid addition salts. Alternatively compound (I) where $R_3$ or $R_6$ is an electron-withdrawing group can be obtained by condensation of the N-imidazoloaniline (9) with the halogeno derivative (8).

The following examples and tests are intended to illustrate the invention without however implying a limitation.

PREPARATION OF THE
N-ALKYLANILINES (3)

EXAMPLE 1

N-(4-chlorophenylmethyl)-4-cyanoaniline

To a solution of 4-chlorobenzaldehyde (35.69 g, 0.253 mol) in absolute ethanol (250 ml) was added portionwise 4-aminobenzonitrile (30 g, 0.253 mol). The reaction mixture was stirred at room temperature for 3 h, the precipitate was filtered, washed with ether and poured into a 1/1 mixture of THF/ethanol (250 ml). The resulting suspension was ice-cooled, $NaBH_4$ (4.8 g, 0.127 mol) was added portionwise and the reaction mixture was stirred at room temperature for 0.75 h. After addition of acetic acid (3 ml) and water (500 ml), the precipitate was filtered, washed with water and dried to give a white solid (51.27 g, 84%), mp 130° C.

$^1$H-NMR (CDCl$_3$): 4.35 (d, 2H), 4.75 (s, 1H), 6.55 (d, 2H), 7.20–7.50 (m, 6H)

Using the same procedure but replacing the 4-chlorobenzaldehyde by 4-methoxybenzaldehyde, 3-fluoromethoxybenzaldehyde, 4-cyano-N-(4-methoxyphenylmethyl)aniline (mp 109° C.), and 4-cyano-N-(3-fluoro-4-methoxyphenylmethyl)aniline (mp 108° C.) were respectively obtained.

EXAMPLE 2

4-cyano-N-(4-methylphenylmethyl)aniline

A mixture of p-tolualdehyde (40.68 g, 0.338 mol), 4-aminobenzonitrile (40 g, 0.338 mol) and 5% Pd/C (4 g) in absolute ethanol (300 ml) was hydrogenated at room temperature overnight. The reaction mixture was diluted with methylene chloride, filtered on celite and concentrated to dryness. Crystallization from ethanol afforded a white solid (74.9 g, 99%), mp 100° C.

$^1$H-NMR (CDCl$_3$): 2.35 (s, 3H), 4.3 (d, 2H), 4.7 (s, 1H), 6.55 (d, 2H), 7.10–7.30 (m, 4H), 7.35 (d, 2H)

Using the same procedure but replacing the p-tolualdehyde by 4-cyanobenzaldehyde, 3,4-dimethoxybenzaldehyde, 4-cyano-N-(4-cyanophenylmethyl)aniline (mp 156° C.), and 4-cyano-N-(3,4-dimethoxyphenylmethyl)aniline (mp 150° C.) were respectively obtained.

PREPARATION OF N,N-DISUBSTITUTED HYDRAZINES (4)

These are generally prepared according to the procedure described in Tetrahedron 1982, 38(3): 419–423 and Organic Fonctional Group Preparations 1968, 1: 374–376.

EXAMPLE 3

$N^1$-(4-chlorophenylmethyl)-$N^1$-(4-cyanophenyl)hydrazine

To an ice-cooled suspension of 4-cyano-N-(4-chlorophenylmethyl)aniline (30 g, 0.125 mol) in 2 N $H_2SO_4$ (150 ml) was added a solution of sodium nitrite (9.48 g, 0.137 mol) in water (30 ml). The reaction mixture was stirred at room temperature for 2 h. A solution of sodium nitrite (9.48 g, 0.137 mol) in water (30 ml) was added, and the reaction was stirred overnight. A solution of sodium nitrite (6.6 g, 0.095 mol) in water (20 ml) was added and the reaction was stirred for 1 h. After extraction with ethyl acetate, the organic layer was washed successively with a saturated sodium hydrogen carbonate solution, water, brine, dried over sodium sulfate and evaporated under vacuum to give a white solid (30.5 g). To a suspension of the resulting solid in a mixture of ether (60 ml), AcOH (60 ml) and water (60 ml), was added zinc powder (24.5 g, 0.375 mol) at such a rate as to keep the temperature below 35° C. The mixture was stirred for 2 h, AcOH (60 ml), water (60 ml) and zinc (6 g) were added and stirring was maintained for 0.5 h. After addition of ether (200 ml), the reaction mixture was filtered, the inorganic material was washed with ethyl acetate, the product was extracted with ethyl acetate and the organic layer was washed with water, brine and dried over sodium sulfate. The solvents were concentrated under vacuum and crystallization from diisopropyl ether yielded a solid (18.78 g, 58%), mp 90° C.

$^1$H-NMR (CDCl$_3$): 3.75 (s, 2H), 4.69 (s, 2H), 7.05 (d, 2H), 7.15 (d, 2H), 7.35 (d, 2H), 7.49 (d, 2H).

Using the same procedure but replacing the 4-cyano-N-(4-chlorophenylmethyl)aniline by 4-cyano-N-(4-methoxyphenylmethyl)aniline, 4-cyano-N-(3-fluoro-4-methoxyphenylmethyl)aniline, 4-cyano-N-(4-methylphenylmethyl)aniline, 4-cyano-N-(4-cyanophenylmethyl)aniline, 4-cyano-N-(3,4-dimethoxyphenylmethyl)aniline, 4-bromo-N-(4-cyanophenylmethyl)aniline, $N^1$-(4-methoxyphenylmethyl)-$N^1$-(4-cyanophenyl)hydrazine (mp 74° C.), $N^1$-(3-fluoro-4-methoxyphenylmethyl)-$N^1$-(4-cyanophenyl)hydrazine (mp 102° C.), $N^1$-(4-methylphenylmethyl)-$N^1$-(4-cyanophenyl)hydrazine (mp 74° C.), $N^1$-(4-cyanophenylmethyl)-$N^1$-(4-cyanophenyl)hydrazine (mp 215° C.), $N^1$-(3,4-dimethoxyphenylmethyl)-$N^1$-(4-cyanophenyl)hydrazine (mp 134° C.), and $N^1$-(4-cyanophenylmethyl)-$N^1$-(4-bromophenyl)hydrazine (mp 114° C.) were respectively obtained.

EXAMPLE 4

$N^1$-(4-trifluoromethylphenylmethyl)-$N^1$-(4-cyanophenyl)hydrazine

In a nitrogen atmosphere, powdered sodium amide (95%, 4.8 g, 0.117 mol) was introduced with stirring into a flask containing THF (100 ml). The solution was ice-cooled and 4-cyano-phenylhydrazine hydrochloride (prepared following José L. Castro et al. J. Med. Chem. 1994, 37, 3023–3032) (10 g, 0.058 mol) was added portionwise. The ice bath was removed and a stream of nitrogen was passed through the orange suspension over a period of 1 h to remove most of the dissolved ammonia. With ice-cooling, 4-trifluoromethylbenzyl chloride (12 g, 0.062 mol) was added, then the reaction mixture was stirred at room temperature for 1.5 h and poured into water (100 ml). After extraction with ethyl acetate, the organic layer was washed with water, dried over sodium sulfate and evaporated under vacuum. Trituration from diisopropyl ether gave a yellow solid (7.5 g, 43%), mp 98° C.

$^1$H-NMR (CDCl$_3$): 3.8 (s, 2H), 4.8 (s, 2H), 7.05 (d, 2H), 7.33 (d, 2H), 7.5 (d, 2H), 7.6 (d, 2H)

Using the same procedure but replacing the 4-trifluoromethylbenzyl chloride by:

4-fluorobenzonitrile, 4-fluorobenzyl bromide, 4-methylthiobenzyl chloride 3,4-difluorobenzyl chloride, 2,4-difluorobenzyl chloride, 3,5-difluorobenzyl chloride, 4-bromobenzyl bromide, $N^1$-bis-(4-cyanophenyl)hydrazine (mp 222° C.), $N^1$-(4-fluorophenylmethyl)-$N^1$-(4-cyanophenyl)hydrazine (mp 114–115° C.), $N^1$-(4-methylthiophenylmethyl)-$N^1$-(4-cyanophenyl)hydrazine (mp 72° C.), $N^1$-(3,4-difluorophenylmethyl)-$N^1$-(4-cyanophenyl)hydrazine (mp 72° C.), $N^1$-(2,4-difluorophenylmethyl)-$N^1$-(4-cyanophenyl)hydrazine (mp 70° C.), $N^1$-(3,5-difluorophenylmethyl)-$N^1$-(4-cyanophenyl)hydrazine (mp 124° C.), and $N^1$-(4-bromophenylmethyl)-$N^1$-(4-cyanophenyl)hydrazine (mp 90° C.) were respectively obtained.

PREPARATION OF THE IMIDAZOLES OF FORMULA (I)

EXAMPLE 5

4-[N-(1H-imidazol-1-yl)-N-(4-trifluoromethylphenyl)amino]benzonitrile

To a cold solution (10–15° C.) of tBuOK (1.06 g, 0.00895 mol) in DMSO (18 ml) was added portionwise N-(1H-imidazol-1-yl)-4-trifluoromethylaniline (1.85 g, 0.00814 mol) (prepared by desulfurization from the corresponding 2,3-dihydro-1H-imidazol-2-thione, J. G. Schantl, Heterocycles, 37(3), 1873, 1994). The reaction mixture was stirred at room temperature for 1 h, then 4-fluorobenzonitrile (0.936 g, 0.00773 mol) in DMSO (18 ml) was added, the reaction mixture was stirred for 2 h and pourred into water and concentrated sodium hydroxyde solution. The precipitate was collected and dried under vacuum. Flash chromatography on silica gel (toluene/dioxane: 7/3) and crystallization from diisopropyl ether yielded a solid (1.6 g, 60%), mp 104° C.

Analysis Calculated.: C: 62.2; H: 3.38; F: 17.36; N: 17.07; Found: C: 62.22; H: 3.40; F: 17.3; N: 17.1.

$^1$H-NMR (DMSO $d_6$): 6.96 (d, 2H), 7.15 (s, 1H), 7.31 (d, 2H), 7.68 (s, 1H), 7.6–7.85 (m, 4H), 7.87 (s, 1H).

EXAMPLE 6

4-[N-(1H-imidazol-1-yl)-N-(4-trifluoromethylphenylmethyl)amino]benzonitrile a) 4-[N-(2,3-dihydro-1H-imidazol-1-yl-2-thione)-N-(4-trifluoromethylphenylmethyl)amino]benzonitrile To a suspension of $N^1$-(4-trifluoromethylphenylmethyl)-$N^1$-(4-cyanophenyl)hydrazine (7.5 g, 0.025 mol) in ethanol (100 ml) was added dropwise 2,2-dimethoxyethylisothiocyanate (4 g, 0.027 mol) and the reaction mixture was heated to reflux for 2 h. After cooling the solvent was evaporated under vacuum, the resulting residue was poured into 2N $H_2SO_4$ (20 ml) and the suspension was heated to reflux for 0.3 h. After extraction with ethyl acetate, the organic layer was washed with water, dried over sodium sulfate and concentrated under vacuum. Flash chromatography on silica gel (toluene/dioxane: 8/2) and trituration from diisopropyl ether/ethanol afforded a yellow solid (2.7 g, 28%), mp 200° C.

$^1$H-NMR (DMSO $d_6$): 5–5.4 (m, 2H), 6.65 (d, 2H), 6.95 (d, 1H), 7.15 (d, 1H), 7.7 (m, 6H).

b) 4-[N-(1H-imidazol-1-yl)-N-(4-trifluoromethylphenylmethyl)amino]benzonitrile

35% hydrogen peroxide (1.1 ml, 0.035 mol) was added dropwise to an ice-cooled suspension of 4-[N-(2,3-dihydro-1H-imidazol-1-yl-2-thione)-N-(4-trifluoromethylphenylmethyl)amino]benzonitrile (2.7 g, 0.0072 mol) in acetic acid (20 ml). When TLC showed complete reaction, the reaction mixture was diluted with water, adjusted to pH 11 with sodium hydroxide, treated with sodium hydrogen sulfite and extracted with ethyl acetate. The organic layer was dried over sodium sulfate and concentrated under vacuum. Flash chromatography on silica gel (toluene/ethyl acetate: 7/3 then 6/4) and crystallization from diisopropyl ether yielded a solid (1 g, 41%), mp 134° C.

Analysis Calculated.: C: 63.1; H: 3.8; N: 16.3; Found: C: 63.4; H: 3.58; N: 16.3.

$^1$H-NMR (DMSO $d_6$): 5.15 (s, 2H), 6.65 (d, 2H), 7 (s, 1H), 7.4 (s, 1H), 7.5–7.9 (m, 7H).

M+=342

Using the same procedure but replacing the $N^1$-(4-trifluoromethylphenylmethyl)-$N^1$-(4-cyanophenyl) hydrazine by:

$N^1$-(4-chlorophenylmethyl)-$N^1$-(4-cyanophenyl) hydrazine,
$N^1$-(4-methoxyphenylmethyl)-$N^1$-(4-cyanophenyl) hydrazine,
$N^1$-(3-fluoro-4-methoxyphenylmethyl-$N^1$-(4-cyanophenyl)hydrazine,
$N^1$-(4-methylphenylmethyl)-$N^1$-(4-cyanophenyl) hydrazine,
$N^1$-(4-cyanophenylmethyl)-$N^1$-(4-cyanophenyl) hydrazine,
$N^1$-(3,4-dimethoxyphenylmethyl)-$N^1$-(4-cyanophenyl) hydrazine,
$N^1$-bis-(4-cyanophenyl)hydrazine,
$N^1$-(4-fluorophenylmethyl)-$N^1$-(4-cyanophenyl) hydrazine,
$N^1$-(4-methylthiophenylmethyl)-$N^1$-(4-cyanophenyl) hydrazine,
$N^1$-(3,4-difluorophenylmethyl)-$N^1$-(4-cyanophenyl) hydrazine,
$N^1$-(2,4-difluorophenylmethyl)-$N^1$-(4-cyanophenyl) hydrazine,
$N^1$-(3,5-difluorophenylmethyl)-$N^1$-(4-cyanophenyl) hydrazine,
$N^1$-(4-bromophenylmethyl)-$N^1$-(4-cyanophenyl) hydrazine,
$N^1$-(4-cyanophenylmethyl)-$N^1$-(4-bromophenyl) hydrazine,
$N^1$-(4-cyanophenylmethyl)-$N^1$-(1-methylbenzotriazol-6-yl)hydrazine,
$N^1$-(4-cyanophenylmethyl)-$N^1$-(3-trifluoromethyl-4-cyanophenyl)hydrazine,
$N^1$-(phenylmethyl)-$N^1$-(4-cyanophenyl)hydrazine,
$N^1$-(4-cyanophenyl)-$N^1$-(3-trifluoromethylcyanophenyl) hydrazine,
$N^1$-(3-fluorophenylmethyl)-$N^1$-(4-cyanophenyl) hydrazine,
$N^1$-(4-methoxycarbonylphenylmethyl)-$N^1$-(4-cyanophenyl)hydrazine,
$N^1$-(4-cyanophenyl)-$N^1$-(4-fluorophenyl)hydrazine,
$N^1$-(3-trifluoromethylphenylmethyl)-$N^1$-(4-cyanophenyl) hydrazine, the following compounds were respectively obtained:

EXAMPLE 7

4-[N-(1H-imidazol-1-yl)-N-(4-chlorophenylmethyl) amino]benzonitrile, hydrochloride mp 190° C.;

Analysis Calculated: C: 59.15; H: 4.09; Cl: 20.54; N: 16.23. Found: C: 59.04; H: 3.99; Cl: 20.5; N: 16.2.

$^1$H-NMR (DMSO $d_6$): 5.15 (s, 2H), 6.95 (d, 2H), 7.4 (s, 4H), 7.75 (m, 3H), 8.10 (s, 1H), 9.6 (s, 1H).

EXAMPLE 8

4-[N-(1H-imidazol-1-yl)-N-(4-methoxyphenylmethyl)amino]benzonitrile, hydrochloride mp 178° C.;

Analysis Calculated: C: 63.44; H 5.03; Cl: 10.40; N: 16.44; Found: C: 63.4; H: 5.01; Cl: 10.4; N: 16.6.

$^1$H-NMR (DMSO $d_6$): 3.70 (s, 3H), 5.05 (s, 2H), 6.85 (d, 2H), 7 (d, 2H), 7.25 (d, 2H), 7.79 (s, 1H), 7.80 (d, 2H), 8.1 (s, 1H), 9.50 (s, 1H).

EXAMPLE 9

4-[N-(1H-imidazol-1-yl)-N-(3-fluoro-4-methoxyphenylmethyl)amino]benzonitrile, hydrochloride mp 190° C.;

$^1$H-NMR (DMSO $d_6$): 3.80 (s, 3H), 5.05 (s, 2H), 7 (d, 2H), 7.05–7.15 (m, 2H), 7.30 (d, 1H), 7.8 (d, 2H), 7.75 (s, 1H), 8.1 (s, 1H), 9.50 (s, 1H).

EXAMPLE 10

4-[N-(1H-imidazol-1-yl)-N-(4-methylphenylmethyl)amino]benzonitrile mp 156° C.;

Analysis Calculated: C: 74.98; H: 5.59; N: 19.43; Found: C: 74.55; H: 5.56; N: 19.3.

$^1$H-NMR (DMSO $d_6$): 2.25 (s, 3H), 4.95 (s, 2H), 6.65 (d, 2H), 6.98 (s, 1H), 7.10 (d, 2H), 7.2 (d, 2H), 7.35 (s, 1H), 7.70 (m, 3H).

EXAMPLE 11

4-[N-(1H-imidazol-1-yl)-N-(4-cyanophenylmethyl)amino]benzonitrile, hydrochloride mp 195° C.;

Analysis: Calculated: C: 64.38; H: 4.2; Cl: 10.56; N: 20.86. Found: C: 64.31; H: 4.29; Cl: 10.6; N: 20.9.

$^1$H-NMR (DMSO $d_6$): 5.30 (s, 2H), 7.10 (d, 2H), 7.62 (d, 2H), 7.70–8 (m, 5H), 8.17 (s, 1H), 9.7 (s, 1H).

EXAMPLE 12

4-[N-(1H-imidazol-1-yl)-N-(3,4-dimethoxyphenylmethyl)amino]benzonitrile, hydrochloride mp 167° C.;

Analysis Calculated: C: 61.54; H: 5.16; Cl: 9.56; N 15.11. Found: C: 61.39; H: 5.13; Cl: 9.57; N: 15.1.

$^1$H-NMR (DMSO $d_6$): 3.70 (s, 3H), 3.73 (s, 3H), 5 (s, 2H), 6.65–7.15 (m, 5H), 7.75 (s, 1H), 7.80 (d, 2H), 8.10 (s, 1H), 9.5 (s, 1H).

EXAMPLE 13

4,4'-[N-(1H-imidazol-1-yl)amino]bis-benzonitrile, hydrochloride mp 199° C.;

Analysis: Calculated: C: 63.46; H: 3.76; Cl: 11.02; N: 21.76. Found: C: 63.2; H: 3.81; Cl: 11.0; N: 21.9.

$^1$H-NMR (DMSO $d_6$): 7.26 (d, 4H), 7.9 (s, 1H), 7.92 (d, 4H), 8.30 (s, 1H), 9.80 (s, 1H).

EXAMPLE 14

4-[N-(1H-imidazol-1-yl)-N-(4-fluorophenylmethyl)amino]benzonitrile, hydrochloride hemihydrate mp 176–178° C.;

Analysis: Calculated: C: 60.45; H: 4.48; F: 5.62; Cl: 10.5; N: 16.59. Found: C: 60.71; H: 4.64; F:5.54; Cl: 10.6; N: 17.0.

$^1$H-NMR (DMSO $d_6$): 5.15 (s, 2H), 7.2 (t, 2H), 7.4 (q, 2H), 7.8 (s, 1H), 7.0–7.8 (AB, 4H), 9.6 (s, 1H).

EXAMPLE 15

4-[N-(1H-imidazol-1-yl)-N-(4-methylthiophenylmethyl)amino]benzonitrile mp 128° C.;

Analysis: Calculated: C: 67.56; H: 5.03; N: 17.5; S: 10.02; Found: C: 67.12; H: 4.90; N: 17.2; S: 9.51.

$^1$H-NMR (DMSO $d_6$): 2.4 (s, 3H), 5.05 (s, 2H), 6.65 (d, 2H), 7 (s, 1H), 7.15–7.3 (m, 4H), 7.35 (s, 1H), 7.7 (m, 3H).

EXAMPLE 16

4-[N-(1H-imidazol-1-yl)-N-(4-methylsulfonylphenylmethyl)amino]benzonitrile $^1$H-NMR (DMSO $d_6$): 3.2 (s, 3H), 5.2 (s, 2H), 6.6 (d, 2H), 7 (s, 1H), 7.45 (s, 1H), 7.6–7.9 (m, 7H).

EXAMPLE 17

4-[N-(1H-imidazol-1-yl)-N-(3,4-difluorophenylmethyl)amino]benzonitrile mp 132° C.;

Analysis Calculated: C: 65.86; H: 3.9; N: 18.07; Found: C: 65.47; H: 3.78; N: 18.1.

$^1$H-NMR (DMSO $d_6$): 5.0 (s, 2H), 6.7 (d, 2H), 6.9–7.8 (m, 8H).

EXAMPLE 18

4-[N-(1H-imidazol-1-yl)-N-(2,4-difluorophenylmethyl)amino]benzonitrile mp 149° C.;

Analysis Calculated: C: 65.86; H: 3.9; N: 18.07; Found: C: 66.0; H: 3.84; N: 18.2.

$^1$H-NMR (DMSO $d_6$): 5.1 (s, 2H), 6.7 (d, 2H), 6.9–7.8 (m, 8H).

EXAMPLE 19

4-[N-(1H-imidazol-1-yl)-N-(3,5-difluorophenylmethyl)amino]benzonitrile mp 170° C.;

Analysis Calculated: C: 65.86; H: 3.9; N: 18.07; Found: C: 65.73; H: 3.8; N: 18.02.

$^1$H-NMR (DMSO $d_6$): 5.1 (s, 2H), 6.6 (d, 2H), 7–7.2 (m, 4H), 7.5 (s, 1H), 7.75 (d, 2H), 7.9 (s, 1H).

EXAMPLE 20

4-[N-(1H-imidazol-1-yl)-N-(4-bromophenylmethyl)amino]benzonitrile, hydrochloride mp 125° C.;

$^1$H-NMR (CDCl$_3$): 5 (s, 2H), 6.8 (d, 2H), 7 (s, 1H), 7.25 (m, 3H), 7.35 (s, 1H), 7.4 (d, 2H), 7.65 (d, 2H), 9.85 (s, 1H).

EXAMPLE 21

4-[N-(1H-imidazol-1-yl)-N-(4-bromophenyl)aminomethyl]benzonitrile mp 138° C.;

Analysis: Calculated: C: 57.81; H: 3.71; N: 15.86; Br: 22.62; Found: C: 57.85; H: 3.7; N: 15.9; Br: 23.2.

$^1$H-NMR (DMSO $d_6$): 4.85 (s, 2H), 6.5 (d, 2H), 7 (s, 1H), 7.1 (s, 1H), 7.25–7.55 (m, 5H), 7.6 (d, 2H).

EXAMPLE 22

4-[N-(1-methylbenzotriazol-6-yl)-N-(1H-imidazol-1-yl)aminomethyl]benzonitrile mp 184° C.;

$^1$H-NMR (DMSO $d_6$): 4.20 (s, 3H), 5.1 (s, 2H), 6.5 (dd, 1H), 6.95 (s, 1H), 7.2 (s, 1H), 7.4 (s, 1H), 7.57 (d, 2H), 7.7–7.85 (m, 3H), 7.9 (d, 1H).

EXAMPLE 23

4-[N-(1H-imidazol-1-yl)-N-(4-cyanophenylmethyl) amino]-3-trifluoromethylbenzonitrile mp 226° C.;
Analysis: Calculated: C: 62.18; H: 3.29; N: 19.08; Found: C: 61.89; H: 3.35; N: 18.9.
$^1$H-NMR (DMSO $d_6$): 5.25 (s, 2H), 6.8–7.05 (m, 3H), 7.45 (s, 1H), 7.55 (d, 2H), 7.8 (d, 3H), 8.05 (d, 1H).

EXAMPLE 24

4-[N-(1H-imidazol-1-yl)-N-(phenylmethyl)amino] benzonitrile mp 107° C.
$^1$H-NMR (DMSO $d_6$): 5.05 (s, 2H), 6.65 (d, 2H), 7 (s, 1H), 7.25–7.4 (m, 6H), 7.65–7.75 (m, 3H).

EXAMPLE 25

4-[N-(1H-imidazol-1-yl)-N-(4-cyanophenyl)amino]-3-trifluoromethylbenzonitrile mp 166° C.;
$^1$H-NMR (DMSO $d_6$): 7.2 (m, 3H), 7.3 (d, 2H), 7.75 (s, 1H), 7.95 (d, 2H), 8.15 (d, 1H), 8.25 (s, 1H).

EXAMPLE 26

4-[N-(1H-imidazol-1-yl)-N-(3-fluorophenylmethyl) amino]benzonitrile mp 112° C.;
Analysis Calculated: C: 69.9; H: 4.48; N: 19.18; Found: C: 69.38; H: 4.35; N: 19.3.
$^1$H-NMR (DMSO $d_6$): 5.05 (s, 2H), 6.65 (d, 2H), 7 (s, 1H), 7.05–7.25 (m, 3H), 7.3–7.45 (m, 2H), 7.7–7.85 (m, 3H).

EXAMPLE 27

Methyl 4-[N-(4-cyanophenyl)-N-(1H-imidazol-1-yl) aminomethyl]benzoate mp 178° C.;
$^1$H-NMR (DMSO $d_6$): 3.85 (s, 3H), 5.15 (s, 2H), 6.65 (d, 2H), 7 (s, 1H), 7.4 (s, 1H), 7.5 (d, 2H), 7.65–7.8 (m, 3H), 7.9 (d, 2H).

EXAMPLE 28

4-[N-(1H-imidazol-1-yl)-N-(4-fluorophenyl)amino] benzonitrile mp 113° C.;
$^1$H-NMR (DMSO $d_6$): 6.45 (d, 2H), 7.1 (s, 1H), 7.25–7.45 (m, 2H), 7.5–7.7 (m, 5H), 8.2 (s, 1H).

EXAMPLE 29

4-[N-(1H-imidazol-1-yl)-N-(3-trifluoromethylphenylmethyl)amino]benzonitrile mp 122° C.;
$^1$H-NMR (DMSO $d_6$): 5.15 (s, 2H), 6.7 (d, 2H), 7 (s, 1H), 7.4 (s, 1H), 7.5–7.8 (m, 7H).

Using the same procedure of Example 6 but replacing the 2-isocyanatoacetaldehyde dimethylacetal by:

2-isothiocyanatoproplonaldehyde diethylacetal,
1-isothiocyanatopropan-2-one diethylacetal,
2-isothiocyanatobutan-3-one diethylacetal, the following compounds were obtained:

EXAMPLE 30

4-[N-(4-methyl-1H-imidazol-1-yl)-N-(4-bromophenylmethyl)amino]benzonitrile mp 152° C.;
Analysis: Calculated: C: 58.9; H: 4.11; N: 15.26; Found: C: 58.67; H: 4.16; N: 15.3.
$^1$H-NMR (DMSO $d_6$): 2.1 (s, 3H), 5 (s, 2H), 6.65 (d, 2H), 7.05 (s, 1H), 7.3 (d, 2H), 7.5 (d, 2H), 7.6 (s, 1H), 7.7 (d, 2H).
M+=366.

EXAMPLE 31

4-[N-(5-methyl-1H-imidazol-1-yl)-N-(4-bromophenylmethyl)amino]benzonitrile mp 152° C.
$^1$H-NMR (CDCl$_3$): 2 (s, 3H), 4.9–5.2 (m, 2H), 6.65 (d, 2H), 7 (s, 1H), 7.25 (d, 2H), 7.5 (d, 2H), 7.6 (d, 2H), 9.25 (s, 1H).
M+=366.

EXAMPLE 32

4-[N-(4,5-dimethyl-1H-imidazol-1-yl)-N-(4-bromophenylmethyl)amino]benzonitrile mp 150° C.;
Analysis Calculated: C: 59.8; H: 4.49; N: 14.7; Found: C: 58.7; H: 4.41; N: 14.6.
$^1$H-NMR (DMSO $d_6$): 1.9 (s, 3H), 2.1 (s, 3H), 4.95–5.25 (m, 2H), 6.6 (d, 2H), 7.3–7.8 (m, 7H).
M+=380.

BIOLOGICAL TEST RESULTS

In Vitro Testing

The JEG-3 cell line, derived from a human placental choriocarcinoma, is intrinsically very rich in human aromatase (Bahn R S et al., J Clin Endocrinol Metab, 1981, 52: 447–450) and, therefore, a useful practical biological system to screen and evaluate putative aromatase inhibitors in vitro (Yue W and Brodie A M, J Steroid Biochem Mol Biol, 1997, 63: 317–328). Stocks of JEG-3 cells are grown up to 80% of confluence as monolayers in plastic flasks in minimum Eagle's medium with 1 g/l glucose and 10% decomplemented fetal calf serum at pH 7.4 and 37° C., under a 5% CO$_2$ atmosphere. Then, 24 hours before aromatase activity measurement, JEG-3 cells are distributed for seeding in 96-well microplates (60,000 to 100,000 viable cells in 100 µl of culture medium per well); 24 hours later, microplates are rinsed and fresh medium containing the radioactive aromatase substrate (1β-$^3$H-androstenedione, 10 nM) is added together with test compounds dissolved with 1% dimethylsulfoxide in a test concentration range between $10^{-11}$ and $10^{-4}$ M in a total volume of 150 µl.

Two hours after the beginning of the incubation, 100 µl of the supernatants are transferred to homologous new 96-well microplates. A solution of dextran-coated charcoal (1%) is added in each well (100 µl/well); after standing for 10 minutes on ice, microplates are centrifuged (1500 g) for 10 more minutes at 4° C. All steroids, including the radioactive substrate and the newly biosynthesized estrogens, are trapped complexed by the charcoal; only the $^3$H-water specifically formed during aromatisation of 1β-$^3$H-androstenedione, involving a specific oxidative step removing the 1β-$^3$H, remains in the supernatant at this stage. Transferred to another homologous 96-well microplate, the 100 μl supernatants receive some scintillation counting liquid (200 μl/well) for β-radioactivity measurement by a Microbeta Plus 1450 microplate Counter (Wallac, EG & G).

In parallel, the aromatase reaction is stopped in the cell-containing microplates by destruction and solubilization of the JEG-3 cells in a 10 mM ethylenediamine tetraacetate solution at pH 12.3. Then, DNA is measured by a standard fluorimetric method using the Hoechst 33258 fluorochrome and a Victor$^2$ (Wallac, EG & G) microplate fluorimeter.

Finally, aromatase activity is expressed in fmoles/μg DNA in 2 hours and aromatase inhibition in percentage of control incubation without inhibitors. A non linear fit analysis of % of inhibition vs. concentration allows the determination of 50% inhibitory concentration (IC$_{50}$): the lowest IC$_{50}$ correspond to the most potent inhibitors (Table A).

TABLE A

Inhibition of human aromatase in vitro

| Compound | IC$_{50}$ ± sem (nM) | n |
|---|---|---|
| Anastrozole | 8.21 ± 1.27 | 3 |
| Example 28 | 1.57 ± 0.74 | 3 |
| Example 30 | 1.16 ± 0.55 | 3 |
| Example 21 | 1.12 ± 0.55 | 3 |
| Example 25 | 0.66 ± 0.14 | 3 |
| Example 31 | 0.58 ± 0.18 | 3 |
| Letrozole | 0.56 ± 0.10 | 12 |
| Example 5 | 0.54 ± 0.26 | 3 |
| Example 23 | 0.48 ± 0.13 | 3 |
| Example 13 | 0.44 ± 0.04 | 3 |
| Example 19 | 0.40 ± 0.06 | 3 |
| Example 16 | 0.35 ± 0.07 | 3 |
| Example 6 | 0.31 ± 0.01 | 3 |
| YM 511 | 0.30 ± 0.04 | 3 |
| Example 17 | 0.24 ± 0.02 | 3 |
| Example 20 | 0.22 ± 0.05 | 3 |
| Example 15 | 0.21 ± 0.05 | 3 |
| Example 22 | 0.20 ± 0.05 | 3 |
| Example 29 | 0.19 ± 0.05 | 3 |
| Example 11 | 0.18 ± 0.02 | 3 |
| Example 24 | 0.18 ± 0.09 | 3 |
| Example 9 | 0.16 ± 0.06 | 3 |
| Example 14 | 0.16 ± 0.02 | 3 |
| Example 7 | 0.14 ± 0.05 | 3 |
| Example 8 | 0.14 ± 0.05 | 3 |
| Example 10 | 0.14 ± 0.03 | 3 |
| Example 18 | 0.14 ± 0.01 | 3 |
| Example 26 | 0.13 ± 0.05 | 3 |

INHIBITION OF AROMATASE IN VIVO

Aromatase is the steroidogenic enzyme responsible for the biosynthesis of estradiol, the main female sex hormone among estrogens. In the rat, estradiol is physiologically synthesized to high circulating levels in a particular period during the 4-day estrous cycle: it is the so-called preovulatory surge taking place in the afternoon of proestrus, just before ovulation which occurs during the night between proestrous and estrous phases. A sensitive physiological model for in vivo evaluation of aromatase inhibition was developped based on the inhibition of this preovulatory surge of estradiol levels.

Adult female Wistar rats are monitored for regular 4-day estrous cyclicity by daily vaginal smear examination; after 2 or 3 regular cycles, animals are treated by a single oral administration of the very low discriminative dose of 10 micrograms/kg in a 4 ml/kg volume around 04:00 PM on diestrus, i.e. on the day before proestrus. Precisely 24 hours later, aortic blood samples are drawn under gaseous anesthesia. Plasma estradiol levels are measured by radioimmunoassay with commercially available kits (Diagnostic Systems Laboratories, Webster, Tex., U. S. A.). Control and test groups usually consist of 7 to 10 rats, depending on the number of regularly cycling rats to distribute among study groups. Results are expressed in pg/ml and then in % of inhibition taking the estradiol levels of control animals receiving only the oral vehicle as the 100% reference to allow comparisons between different independent studies, since the preovulatory surge level may vary in each control group from one study to another between about 25 to 40 pg/ml.

TABLE B

Inhibition of aromatase in vivo

| Compound | % inhibition at 10 μg/kg | n |
|---|---|---|
| Anastrozole | 18%–33% | 2 |
| YM 511 | 35% | 1 |
| Example 7 | 47% | 1 |
| Example 14 | 49%–57% | 2 |
| Example 6 | 57% | 1 |
| Example 11 | 57%–59% | 2 |
| Example 17 | 60% | 1 |

It can be seen that compounds falling within the general formula (I) according to the present invention induce a slightly or markedly higher inhibition of estradiol biosynthesis due to inhibition of aromatase in vivo than does YM 511, taken as a structural reference of N-triazole (Okada et al., Chem Pharm Bull, 1996, 44: 1871–1879), or anastrozole, a standard antiaromatase already used therapeutically. The compounds failing within the general formula (I) thus represent a substantial improvement over the latter substances.

In vivo data (Table B) were not absolutely correlated with in vitro data (Table A) but, taken as a whole, both sets of biological results indicate that the series of 1-N-phenylamino-1H-imidazole derivatives according to the present invention yields numerous nanomolar and subnanomolar inhibitors of aromatase among which several exert effective in vivo inhibition of estrogen biosynthesis. These compounds are therefore useful for counteracting or managing pathological or physiological estrogen-dependent mechanisms, preferentially in females (women or female animals) but also in males (men or male animals).

What is claimed is:

1. A derivative of formula (I):

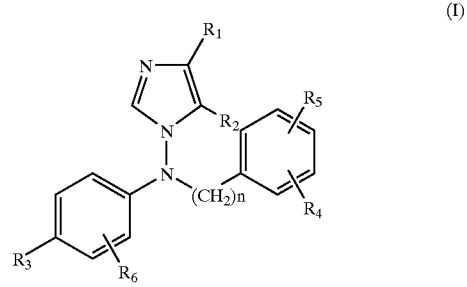

and acid addition salts, solvates and stereoisomeric forms thereof, wherein:

R$_1$ and R$_2$ are each independently hydrogen, a (C$_1$–C$_6$) alkyl or (C$_3$–C$_8$)cycloalkyl;

n is 0, 1, or 2;

$R_3$, $R_4$, $R_5$ and $R_6$ are each independently hydrogen, or a ($C_1$–$C_6$)alkyl, halogen, cyano, ($C_1$–$C_6$)alkoxy, trifluoromethyl, ($C_1$–$C_6$)alkylthio, ($C_1$–$C_6$) alkylsulfonyl, sulfonamido, acyl, ($C_1$–$C_6$) alkoxycarbonyl, or carboxamido group;

$R_3$ and $R_6$ together with the phenyl ring bearing them can also form a benzofurane, or a N-methylbenzotriazole.

2. A derivative according to claim 1, wherein:

n is 0 or 1;

$R_1$ and $R_2$ are each independently hydrogen or ($C_1$–$C_6$) alkyl;

$R_3$ is cyano or trifluoromethyl;

$R_4$ is hydrogen, ($C_1$–$C_6$)alkyl, halogen, cyano, ($C_1$–$C_6$) alkoxy, trifluoromethyl, ($C_1$–$C_6$)alkylthio, ($C_1$–$C_6$) alkylsulfonyl or ($C_1$–$C_6$)alkoxycarbonyl;

$R_5$ is hydrogen, halogen, ($C_1$–$C_6$)alkoxy or trifluoromethyl;

$R_6$ is hydrogen;

or $R_3$ and $R_6$ together with the phenyl ring bearing them form a N-methylbenzotriazole;

and acid addition salts, solvates and stereoisomeric forms thereof.

3. A derivative according to claim 1, wherein:

n is 0 or 1;

$R_1$, $R_2$ and $R_6$ are each hydrogen;

$R_4$ is halogen, cyano or trifluoromethyl;

and acid addition salts, solvates and stereoisomeric forms thereof.

4. A derivative according to claim 1, wherein $R_3$ is cyano; and acid addition salts, solvates and stereoisomeric forms thereof.

5. A derivative according to claim 1, wherein $R_5$ is hydrogen or trifluoromethyl;

and acid additions salts, solvates and stereoisomeric forms thereof.

6. A derivative according to claim 1, wherein n is 1; and acid addition salts, solvates and stereoisomeric forms thereof.

7. A pharmaceutical composition comprising a derivative according to claim 1, or a pharmaceutically acceptable acid addition salt thereof, and a pharmaceutical acceptable carrier.

8. A pharmaceutical composition according to claim 7, which is an aromatase inhibitor composition.

9. A pharmaceutical composition according to claim 7, comprising from 1 to 100 mg of said derivative.

10. A derivative according to claim 2, wherein:

n is 0 or 1;

$R_1$, $R_2$ and $R_6$ are each hydrogen;

$R_4$ is halogen, cyano or trifluoromethyl;

and acid addition salts, solvates and stereoisomeric forms thereof.

11. A derivative according to claim 2, wherein $R_3$ is cyano;

and acid addition salts, solvates and stereoisomeric forms thereof.

12. A derivative according to claim 3, wherein $R_3$ is cyano;

and acid addition salts, solvates and stereoisomeric forms thereof.

13. A derivative according to claim 2, wherein $R_5$ is hydrogen or trifluoromethyl;

and acid additions salts, solvates and stereoisomeric forms thereof.

14. A derivative according to claim 3, wherein $R_5$ is hydrogen or trifluoromethyl;

and acid additions salts, solvates and stereoisomeric forms thereof.

15. A derivative according to claim 4, wherein $R_5$ is hydrogen or trifluoromethyl;

and acid additions salts, solvates and stereoisomeric forms thereof.

16. A derivative according to claim 2, wherein n is 1; and acid addition salts, solvates and stereoisomeric forms thereof.

17. A derivative according to claim 3, wherein n is 1; and acid addition salts, solvates and stereoisomeric forms thereof.

18. A derivative according to claim 4, wherein n is 1; and acid addition salts, solvates and stereoisomeric forms thereof.

19. A derivative according to claim 5, wherein n is 1; and acid addition salts, solvates and stereoisomeric forms thereof.

20. A pharmaceutical composition comprising a derivative according to claim 2, or a pharmaceutically acceptable acid addition salt thereof, and a pharmaceutical acceptable carrier.

21. A pharmaceutical composition comprising a derivative according to claim 3, or a pharmaceutically acceptable acid addition salt thereof, and a pharmaceutical acceptable carrier.

22. A pharmaceutical composition comprising a derivative according to claim 4, or a pharmaceutically acceptable acid addition salt thereof, and a pharmaceutical acceptable carrier.

23. A pharmaceutical composition comprising a derivative according to claim 5, or a pharmaceutically acceptable acid addition salt thereof, and a pharmaceutical acceptable carrier.

24. A pharmaceutical composition comprising a derivative according to claim 6, or a pharmaceutically acceptable acid addition salt thereof, and a pharmaceutical acceptable carrier.

25. A method of treating estrogen-dependent tumors, which comprises administering to a subject in need thereof an effective amount of a compound according to claim 1, or a pharmaceutically acceptable acid addition salt thereof.

26. The method according to claim 25, wherein said derivative is administered in combination with a sexual endocrine therapeutic agent.

27. A method of controlling or managing reproductive functions, which comprises administering to a subject in need thereof an effective amount of a compound according to claim 1, or a pharmaceutically acceptable acid addition salt thereof.

28. The method according to claim 27, wherein said derivative is administered in combination with a LH-RH agonist or antagonist, an estroprogestative contraceptive, a progestin, an anti-progestin or a prostaglandin.

29. A method of treating benign or malignant tumors of the breast, the uterus or the ovary, which comprises administering to a subject in need thereof an effective amount of a compound according to claim 1, or a pharmaceutically acceptable acid addition salt thereof.

30. The method according to claim 29, wherein said derivative is administered in combination with an anti-estrogen, a progestin or a LH-RH agonist or antagonist.

31. A method of treating benign or malignant tumors of the prostate or the testis, which comprises administering to a subject in need thereof an effective amount of a compound according to claim 1, or a pharmaceutically acceptable acid addition salt thereof.

32. The method according to claim 31, wherein said derivative is administered in combination with an antiandrogen, a progestin, a lyase inhibitor or a LH-RH agonist or antagonist.

* * * * *